(12) United States Patent
Kenny

(10) Patent No.: US 7,416,535 B1
(45) Date of Patent: Aug. 26, 2008

(54) NEOPLASTIC CELL DESTRUCTION DEVICE AND METHOD UTILIZING LOW FREQUENCY SOUND WAVES TO DISRUPT OR DISPLACE CELLULAR MATERIALS

(76) Inventor: Daniele Kenny, 8 Braemer Rd., East Seatauket, NY (US) 11733

( * ) Notice: Subject to any disclaimer, the term of this patent is extended or adjusted under 35 U.S.C. 154(b) by 611 days.

(21) Appl. No.: 08/777,452

(22) Filed: Dec. 30, 1996

(51) Int. Cl.
*A61N 7/00* (2006.01)

(52) U.S. Cl. .......................................................... 601/2
(58) Field of Classification Search .................. 601/2–4; 604/22; 600/439
See application file for complete search history.

(56) References Cited

U.S. PATENT DOCUMENTS

| | | | | |
|---|---|---|---|---|
| 5,095,890 A | * | 3/1992 | Houghton et al. | 601/2 |
| 5,143,063 A | * | 9/1992 | Fellner | 601/2 |
| 5,178,134 A | * | 1/1993 | Vago | 601/2 |
| 5,209,221 A | * | 5/1993 | Riedlinger et al. | 601/2 |
| 5,435,311 A | * | 7/1995 | Umemura et al. | 600/439 |
| 5,501,655 A | * | 3/1996 | Rolt et al. | 601/3 |
| 5,549,544 A | * | 8/1996 | Young et al. | 601/2 |
| 5,558,623 A | * | 9/1996 | Cody | 601/2 |
| 5,713,848 A | * | 2/1998 | Dubrul et al. | 604/22 |

* cited by examiner

*Primary Examiner*—Ruth S Smith
(74) *Attorney, Agent, or Firm*—Bernard S. Hoffman

(57) ABSTRACT

A neoplasm cell destruction device utilizing low frequency sound waves to disrupt or displace cellular materials in neoplastic cells so as to damage and ultimately destruct the neoplastic cells without destructing surrounding healthy cells and thereby eliminating the need for target finding apparatus. The device includes a plurality of signal generators, a controller, a plurality of amplifiers, a plurality of transducers, and a target interface. The controller is in electrical communication with, and generates timing and control signals for simultaneously activating, the plurality of signal generators. Each amplifier is in electrical communication with a respective signal generator and amplifies the signal generated by the respective signal generator so as to form an amplified signal. Each transducer is in electrical communication with a respective amplifier and is driven by the amplified signal formed by the respective amplifier. The target interface combines the waveform formed by the plurality of transducers to form an interference wave which is a low frequency sound wave.

13 Claims, 12 Drawing Sheets

NEOPLASTIC CELL DESTRUCTION DEVICE AND METHOD UTILIZING LOW FREQUENCY SOUND WAVES TO DISRUPT OR DISPLACE CELLULAR MATERIALS

BACKGROUND OF THE INVENTION

1. Field of the Invention

The present invention relates to a biological cell destruction device. More particularly, the present invention relates to a neoplasm cell destruction device utilizing low frequency sound waves to disrupt or displace cellular materials in neoplastic cells so as to damage and ultimately destruct the neoplastic cells without destructing surrounding healthy cells by virtue of the neoplastic cells trading in their ability to heal themselves if damaged in return for uncontrollable reproduction whereas the healthy cells can repair themselves if damaged and thereby eliminating a need for target finding apparatus.

2. Description of the Prior Art

High frequency acoustic waves or ultrasound may be used to remotely heat industrial or biological materials. There has been strong evidence in research and clinical laboratories that focused ultrasound for cancer hyperthermia will become a useful mode of treating cancer patients, in addition to the surgical, radiological, and chemotherapeutic methods that are available now.

In the treatment of tumors in cancer hyperthermia, focused ultrasound heats the tumor to a temperature of approximately 43° C. while the adjacent healthy tissue is kept at a lower temperature, closer to normal body temperature (37° C.). The elevated temperature in the tumor disrupts the tumor growth and eventually kills it. This allows the cancer to potentially be treated without surgery, without ionizing radiation, or without chemotherapy.

Conventional focused ultrasound for heating is employed by using either a scanned ultrasound transducer or with a phased array. The scanned transducer uses a lens, much like an optical magnifying glass focus sunlight, while the phased array uses electronic delays among the array elements to achieve focusing. A burst of sound is then emitted which converges at the focus to provide localized high intensity acoustic energy. Some of the high energy acoustic energy is absorbed by the tissue at the focus and is dissipated as concentrated focal heat. The rest of the energy travels through the focus and is slowly dissipated into the surrounding tissues as distributed heat.

Biomedical hyperthermia applicators using a plurality of sound sources to heat larger, distributed volumes, have also been investigated. These investigations have relied upon linear thermal superposition of the plurality of sound sources to heat the target tissue. Nonlinear effects of sound propagation through animal tissue and materials have also been studied for a single sound source.

The nonlinear mixing, or intermodulation, of sound waves has been known in oceanographic acoustics. Oceanographic acoustic applications have used both the linear (superposition) and the nonlinear (intermodulation) effects of intersecting sound beams. Nonlinear acoustic sonars, known as oceanographic parametric sonars, deliberately promote the generation of a difference frequency to enhance sonar beam forming and long range sound propagation. The generated difference frequency is usually 30 to 60 dB below the level of the primary frequencies. A second product of nonlinear mixing is the sum frequency, which is generated by the intermodulation process at 10 to 40 dB below the level of the primary frequencies, indicating that the conversion from primary to sum frequency is a significantly more efficient process than the conversion of a primary to a difference frequency. Since higher frequencies are subject to higher absorption coefficients in water, they generate more heat than the primary frequencies as they propagate, but propagate shorter distances than the primary frequencies. In oceanographic sonar applications, heat generation via sound absorption is generally an undesirable result of nonlinear intermodulation.

It is generally recognized that the use of microwave energy to produce moderate internal heating is an effective tool in the treatment of tissue, especially neoplastic tumors. The primary factor limiting such treatment in the past has been the difficulty of delivering the heat to a target region below the skin surface. Of course, it is possible to use an interstitial source, but this method has the drawback of being invasive. Because of this limitation, noninvasive treatment to date has largely been confined to treatment of surface tumors since it is difficult to heat deep tumors without also heating the intervening tissue.

In order to get significant heating in tumors more than a few millimeters below the skin surface, the field from a single source at the skin surface will have to be high and therefore painful. One approach has used a moving source, generally activated by switching discrete sub-arrays of sources. The moving source, however, results in an incoherent summation of energy at the tumor site. While tending to reduce the heating effects in the intervening tissue, this method has not eliminated the heating of the intervening tissue or reduced it to an acceptable level.

Additionally, to insure that the desired volume of tissue is potentially heated, an operator must not only know the characteristics in the area of interest, but also be able to determine which tissues are being heated. Currently, the ability to make this determination depends on the use of an interstitial probe or a radiometer. The current method also does not allow for imaging of the area, except to use other modalities, such as CT, MRI, ultrasound, etc. Such methods, while noninvasive, do not provide appropriate characteristics of the area and tissue to maximize the heating of the target tissue with microwaves.

Most cancer cells during metastasis are rapidly killed by mechanical trauma, associated with shape-transitions, which requires increases in cell surface area. L. Weiss, J. P. Harlos, and G. Elkin; Int. J. Cancer 44; 143-148 (1989).

The hypothesis has been advanced that such increases in surface area occur in two phases. First, there is an apparent increase as a result of surface unfolding, which is reversible and non-lethal. Second, there is a true increase, during which cell surface membranes are stretched, with an increase in membrane tension. When tension exceeds a critical level, the surface membranes rupture and the irreversible change is lethal.

Numerous innovations for destroying biological tissues have been provided in the prior art that will be described. Even though these innovations may be suitable for the specific individual purposes to which they address, however, they differ from the present invention in that they do not teach a cancer cell destruction device utilizing low frequency sound waves to disrupt or displace cellular materials in cancerous cells so as to damage and ultimately destruct the cancerous cells without destructing surrounding healthy cells by virtue of the cancerous cells trading in their ability to heal themselves if damaged in return for uncontrollable reproduction whereas the healthy cells can repair themselves if damaged and thereby eliminating the need for target finding apparatus.

For example, U.S. Pat. No. 5,144,953 to Wurster et al. teaches a lithotritor with an X-ray alignment system that includes a transducer for generating focused ultrasonic shock waves adapted for alignment on a concretion or tissue to be destroyed. The transducer is connected to an image-forming diagnostic X-ray system for locating the concretion or tissue and includes an X-ray emitter and an image intensifier disposed on a pivotable frame. The transducer is connected to the X-ray emitter which in turn is disposed at the center of the transducer, so that the emission axes of the transducer and the X-ray emitter coincide.

Another example, U.S. Pat. No. 5,222,484 to Krauss et al. teaches an apparatus for shock wave treatment that includes a shock wave transducer with a cup-shaped body and with an X-ray location finding device for finding the location of a bodily concretion or tissue to be treated. The X-ray device includes an extendable X-ray tube with telescoping tube sections which are sealed against an acoustic coupling medium filling the delay path of the transducer by a balloon filling arranged within the X-ray tube. The balloon is secured to the upper section of the tube and to the lower section thereof. Over pressure or under pressure is applied to the interior of the X-ray tube to adjust its length in order to optimize X-ray location finding on the one hand, and shock wave treatment on the other hand.

Still another example, U.S. Pat. No. 5,388,581 to Bauer et al. teaches a therapy apparatus for treating concretions and tissue in the body of a patient by means of sound waves. The apparatus includes a sound wave generator and an available X-ray device for locating an object for therapy. The therapy apparatus has a spot film device that is arranged within the axial passage of an X-ray cone. The available X-ray device is attached to the sound wave generator, with its central longitudinal axis aligned with the focus thereof so as to be able to precisely adjust and fix the X-ray device to the therapy apparatus quickly and safely.

Yet another example, U.S. Pat. No. 5,498,236 to Dubrul et al. teaches a catheter suitable for introduction into a tubular tissue for dissolving blockages in such tissue. The catheter is particularly useful for removing thrombi within blood vessels. In accordance with the preferred embodiments, a combination of vibrating motion and injection of a lysing agent is utilized to break up blockages in vessels. The vessels may be veins, arteries, ducts, intestines, or any lumen within the body that may become blocked from the material that flows through it. As a particular example, dissolution of vascular thrombi is facilitated by advancing a catheter through the occluded vessel with the catheter causing a vibrating stirring action in and around the thrombus usually in combination with the dispensing of a thrombotic agent, such as urokinase into the thrombus. The catheter has an inflatable or expandable member near the distal tip which when inflated or expanded, prevents the passage of dislodged thrombus around the catheter. The dislodged portions of thrombus are directed through a perfusion channel in the catheter where they are removed by filtration means housed within the perfusion channel before the blood exits the tip of the catheter. Catheters that allow both low frequency (1-1000 Hz) vibratory motion and deliver of such agents to a blockage and a method for using such catheters are disclosed.

Still yet another example, U.S. Pat. No. 5,501,655 to Rolt et al. teaches an ultrasound hyperthermia applicator suitable for medical hyperthermia treatment, and method a for using it. The applicator includes two ultrasound sources producing focused ultrasound beams of frequencies $f_0$ and $f_1$. An aiming device directs the two ultrasound beams, so that they cross each other confocally at the target. A controller activates the two ultrasound sources, so that the target is simultaneously irradiated by the two focused ultrasound beams. The two ultrasound sources provide acoustic energy sufficient to cause sufficient intermodulation products to be produced at the target as a result of the interaction of the two ultrasound beams. The intermodulation products are absorbed by the target to enhance heating of the target. In preferred embodiments, the ultrasound sources include a pair of signal generators for producing gated ultrasound output signals driving single crystal ultrasound transducers. In other embodiments, the ultrasound sources include a pair of phased array ultrasound transducers for generating two separate ultrasound beams. An aiming device is provided for electronically steering and focusing the two ultrasound beams, so that they cross each other confocally at the target. Further embodiments employ pluralities of transducers, arrays, or both.

Yet still another example, U.S. Pat. No. 5,503,150 to Evans teaches a method and apparatus for noninvasively locating and heating a volume of tissue, specifically a cancerous tumor. The method includes placing a bolus in contact with the patient and substantially around an area of interest including the volume of tissue, placing an array of antennas on the bolus and substantially around the area of interest, imaging the area of interest, selecting an approximate center of the volume of tissue on the initial image, determining approximate amplitudes and phases for the antennas, energizing each element at respective appropriate amplitudes and phases to heat the volume of tissue, imaging respectively the area of interest to create subsequent images, and subtracting the initial image from the subsequent images to determine temperature changes in the area of interest.

Still yet another example, U.S. Pat. No. 5,524,625 to Okazaki et al. teaches a shock wave generating system capable a forming a wide concretion-disintegrating region by energizing ring-shaped transducers and a hyperthermia curing system. A width of a focused region synthesized from a plurality of focal points formed by a plurality of shock waves is varied by properly controlling delay times and/or drive voltages for a plurality of ring-shaped piezoelectric transducer elements. The shock wave generating system includes a shock wave generating unit having a plurality of shock wave generating elements and a driving unit for separately driving the plurality of shock wave generating elements by controlling at least delay times to produce a plurality of shock waves in such a manner that a dimension of a focused region synthesized from a plurality of different focal points formed by the plurality of shock waves is varied in accordance with a dimension of a concretion to be disintegrated which is present in a biological body under medical examination.

Finally, yet still another example, U.S. Pat. No. 5,542,906 to Herrman et al. teaches a therapy apparatus that has a source of acoustic waves which generates acoustic waves focused onto a focus and an X-ray locating means with which the subject to be treated can be irradiated from different directions. The central ray of the locating means assumes a first direction for a first irradiation direction and a second direction for a second irradiation direction. The apparatus has a positioning system with which the subject to be treated and the focus can be adjusted relative to one another. The region to be treated and the focus are adjustable relative to one another by synchronous actuation of the positioning system in two adjustment directions for at least one irradiation direction. The adjustment taking place in a direction that proceeds parallel to the direction of the central ray that belongs to the other irradiation direction.

It is apparent that numerous innovations for destroying biological tissues have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

Accordingly, an object of the present invention is to provide a neoplasm cell destruction device utilizing low frequency sound waves to disrupt or displace cellular materials that avoids the disadvantages of the prior art.

Neoplastic cells trade in their ability to heal themselves in return for uncontrollable reproduction. If the neoplasm cells, per se, became damaged, they could therefore not heal themselves and they would therefore eventually be destroyed. It is this verity under which the present invention operates.

The present invention utilizes low frequency sound waves to disrupt or displace cellular materials which damages cells. Healthy cells subjected to this damage, however, can heal themselves whereas neoplastic cells cannot and therefore die. It is this verity which eliminates the need for a location finding device in the present invention and the complexities involved therewith.

Another object of the present invention is to provide a neoplasm cell destruction device utilizing low frequency sound waves to disrupt or displace cellular materials that eliminates the need for a location finding device and the complexities involved therewith.

Still another object of the present invention is to provide a neoplasm cell destruction device utilizing low frequency sound waves to do at least one of disrupt and displace cellular materials in neoplastic cells having resonant frequencies so as to damage and ultimately destruct the neoplastic cells without destructing surrounding healthy cells by virtue of the neoplastic cells trading in their ability to heal themselves if damaged in return for uncontrollable reproduction whereas the healthy cells can repair themselves if damaged and thereby eliminating the need for location finding apparatus.

Briefly stated, yet another object of the present invention is to provide a neoplasm cell destruction device utilizing low frequency sound waves to disrupt or displace cellular materials that includes a plurality of signal generators, a controller, a plurality of amplifiers, a plurality of transducers, and a target interface.

Still yet another object of the present invention is to provide a neoplasm cell destruction device utilizing low frequency sound waves to disrupt or displace cellular materials wherein each signal generator of the plurality of signal generators generates a signal.

Yet still yet another object of the present invention is to provide a neoplasm cell destruction device utilizing low frequency sound waves to disrupt or displace cellular materials wherein the controller is in electrical communication with, and generates timing and control signals for selectively activating, the plurality of signal generators.

Still yet another object of the present invention is to provide a neoplasm cell destruction device utililizing low frequency sound waves to disrupt or displace cellular materials wherein each amplifier of the plurality of amplifiers is in electrical communication with a respective signal generator of the plurality of signal generators and amplifies the signal generated by the respective signal generator of the plurality of signal generators so as to form an amplified signal.

Yet still yet another object of the present invention is to provide a neoplasm cell destruction device utilizing low frequency sound waves to disrupt or displace cellular materials wherein each transducer of the plurality of transducers is in electrical communication with a respective amplifier of the plurality of amplifiers and is driven by the amplified signal formed by the respective amplifier of the plurality of amplifiers.

Still yet another object of the present invention is to provide a neoplasm cell destruction device utilizing low frequency sound waves to disrupt or displace cellular materials wherein each transducer of the plurality of transducers form a waveform that is a low frequency sound wave.

Yet still yet another object of the present invention is to provide a neoplasm cell destruction device utilizing low frequency sound waves to disrupt or displace cellular materials wherein the target interface combines the waveforms formed by the plurality of transducers to form an interference wave which is a low frequency sound wave and which is impactable upon the neoplastic cells and damages and ultimately destructs the neoplastic cells without destructing the surrounding healthy cells by virtue of the neoplastic cells trading in their ability to heal themselves if damaged in return for uncontrollable reproduction whereas the healthy cells can repair themselves if damaged and thereby eliminating the need for location finding apparatus.

Still yet another object of the present invention is to provide a neoplasm cell destruction device utilizing low frequency sound waves to disrupt or displace cellular materials wherein the controller is a microprocessor.

Yet still yet another object of the present invention is to provide a neoplasm cell destruction device utilizing low frequency sound waves to disrupt or displace cellular materials that further includes a user interface that is in electrically communication with the controller.

Still yet another object of the present invention is to provide a neoplasm cell destruction device utilizing low frequency sound waves to disrupt or displace cellular materials wherein the user interface is at least one of a keyboard and a display.

Yet still yet another object of the present invention is to provide a neoplasm cell destruction device utilizing low frequency sound waves to disrupt or displace cellular materials wherein each waveform formed by the plurality of transducers are different, and when combined, provide a synergistic effect in producing the interference wave.

Still yet another object of the present invention is to provide a neoplasm cell destruction device utilizing low frequency sound waves to disrupt or displace cellular materials that further includes a feedback sensor disposed in close proximity to the target interface and in electrical communication with the controller.

Yet still yet another object of the present invention is to provide a neoplasm cell destruction device utilizing low frequency sound waves to disrupt or displace cellular materials wherein the feedback sensor receives a feedback wave emanating from the neoplastic cells when the neoplastic cells are impacted upon by the interference wave and generates a feedback signal in response thereto that is received by the controller which in turn continually compares the feedback signal to the interference wave and automatically adjusts each signal generator of the plurality of signal generators, accordingly, until the interference wave is at the resonant frequencies of the neoplastic cells so as to maximize damage to the neoplastic cells.

Still yet another object of the present invention is to provide a neoplasm cell destruction device utilizing low frequency sound waves to disrupt or displace cellular materials that further includes a feedback sensor disposed in close proximity to the target interface and is in electrical communication with each signal generator of the plurality of signal generators.

Yet still yet another object of the present invention is to provide a neoplasm cell destruction device utilizing low frequency sound waves to disrupt or displace cellular materials wherein the feedback sensor receives a feedback wave emanating from the neoplastic cells when the neoplastic cells are impacted upon by the interference wave and generates a feedback signal in response thereto that is received by each signal generator of the plurality of signal generators which in turn are manually adjusted, accordingly, until the interference wave is at the resonant frequencies of the neoplastic cells so as to maximize damage to the neoplastic cells.

Still yet another object of the present invention is to provide a neoplasm cell destruction device utilizing low frequency sound waves to disrupt or displace cellular materials wherein the target interface includes a tub that defines an internal chamber in which a body of a patient is placeable when the neoplastic cells are wide spread throughout the body of the patient.

Yet still yet another object of the present invention is to provide a neoplasm cell destruction device utilizing low frequency sound waves to disrupt or displace cellular materials wherein the plurality of transducers are disposed on the tub of the target interface, with each waveform emanating therefrom into the internal chamber in the tub of the target interface.

Still yet another object of the present invention is to provide a cancer cell destruction device utilizing low frequency sound waves to disrupt or displace cellular materials wherein the target interface further includes a liquid that is contained in the internal chamber in the tub of the target interface and communicates with both the plurality of transducers and the body of the patient, and functions as an acoustical coupler to combine the waveforms formed by the plurality of transducers to form the interference wave.

Yet still yet another object of the present invention is to provide a neoplasm cell destruction device utilizing low frequency sound waves to disrupt or displace cellular materials wherein the target interface includes a hollow, elongated, and slender, hand-held tubular body that contains an internal chamber, and has a wide proximal end and a tapered distal treatment end, and is holdable in, and orientably controllable by, a hand of a user.

Still yet another object of the present invention is to provide a neoplasm cell destruction device utilizing low frequency sound waves to disrupt or displace cellular materials wherein the hollow, elongated, and slender, hand-held tubular body of the target interface is one of plastic and metal.

Yet still yet another object of the present invention is to provide a neoplasm cell destruction device utilizing low frequency sound waves to disrupt or displace cellular materials wherein the plurality of transducers are disposed at the wide proximal end of the hollow, elongated, and slender, hand-held tubular body of the target interface, with each waveform emanating therefrom emanating into the internal chamber in the hollow, elongated, and slender, hand-held tubular body of the target interface.

Still yet another object of the present invention is to provide a neoplasm cell destruction device utilizing low frequency sound waves to disrupt or displace cellular materials wherein the target interface further includes a diaphragm that is disposed at, and closes, the tapered distal treatment end of the hollow, elongated, and slender, hand-held tubular body of the target interface, and concentrates the interference wave.

Yet still yet another object of the present invention is to provide a neoplasm cell destruction device utilizing low frequency sound waves to disrupt or displace cellular materials wherein the diaphragm of the target interface communicates with the internal chamber in the hollow, elongated, and slender, hand-held tubular body of the target interface and is contactable at least in close proximity to the neoplastic cells when the neoplastic cells are contained in a small area in a body of a patient and pinpoint accuracy is required.

Still yet another object of the present invention is to provide a neoplasm cell destruction device utilizing low frequency sound waves to disrupt or displace cellular materials wherein the target interface further includes a liquid that is contained in the internal chamber in the hollow, elongated, and slender, hand-held tubular body of the target interface, and communicates with both the plurality of transducers and the diaphragm of the target interface, and functions as an acoustical coupler to combine the waveforms formed by the plurality of transducers to form the interference wave.

Yet still yet another object of the present invention is to provide a neoplasm cell destruction device utilizing low frequency sound waves to disrupt or displace cellular materials wherein the target interface includes a hollow and hand-held body that contains an internal chamber, and has an upper wall and a lower treatment wall, and is holdable in a hand of a user that is passable through a loop disposed on the upper wall of the hollow and hand-held body of the target interface.

Still yet another object of the present invention is to provide a neoplasm cell destruction device utilizing low frequency sound waves to disrupt or displace cellular materials wherein the hollow and hand-held body of the target interface is one of plastic and metal.

Yet still yet another object of the present invention is to provide a neoplasm cell destruction device utilizing low frequency sound waves to disrupt or displace cellular materials wherein the plurality of transducers are disposed on any convenient location of the hollow and hand-held body of the target interface that is not obstructive to the loop of the target interface, with the waveforms emanating therefrom into the internal chamber in the hollow and hand-held body of the target interface.

Still yet another object of the present invention is to provide a neoplasm cell destruction device utilizing low frequency sound waves to disrupt or displace cellular materials wherein the target interface further includes a diaphragm that is disposed at, and closes, the lower treatment wall of the hollow and hand-held body of the target interface, and distributes the interference wave.

Yet still yet another object of the present invention is to provide a neoplasm cell destruction device utilizing low frequency sound waves to disrupt or dispute cellular materials wherein the diaphragm of the target interface communicates with the internal chamber in the hollow and hand-held body of the target interface, and is contactable at least in close proximity to the neoplastic target when the neoplasmous cells are contained in a large area in a body of a patient.

Still yet another object of the present invention is to provide a neoplasm cell destruction device utilizing low frequency sound waves to disrupt or displace cellular materials wherein the target interface further includes a liquid that is contained in the internal chamber in the hollow and hand-held body of the target interface, and communicates with both the plurality of transducers and the diaphragm of the target interface, and functions as an acoustical coupler to combine the waveforms formed by the plurality of transducers to form the interference wave.

Yet still yet another object of the present invention is to provide a neoplasm cell destruction device utilizing low frequency sound waves to disrupt or displace cellular materials wherein the target interface includes a catheter that contains an internal chamber, and has a wide proximal end and a distal treatment end.

Still yet another object of the present invention is to provide a neoplasm cell destruction device utilizing low frequency sound waves to disrupt or displace cellular materials wherein the plurality of transducers are disposed at the wide proximal end of the catheter of the target interface, with each waveform emanating therefrom emanating into the internal chamber in the catheter of the target interface.

Yet still yet another object of the present invention is to provide a neoplasm cell destruction device utilizing low frequency sound waves to disrupt or displace cellular materials wherein the target interface further includes a diaphragm that is disposed at, and closes, the distal treatment end of the catheter of the target interface, and concentrates the interference wave.

Still yet another object of the present invention is to provide a neoplasm cell destruction device utilizing low frequency sound waves to disrupt or displace cellular materials wherein the diaphragm of the target interface communicates with the internal chamber in the catheter of the target interface, and is contactable at least in close proximity to the neoplastic cells when the neoplastic cells are contained in a lumen in a body of a patient.

Yet still yet another object of the present invention is to provide a neoplasm cell destruction device utilizing low frequency sound waves to disrupt or displace cellular materials wherein the target interface further includes a liquid that is contained in the internal chamber in the cathether of the target interface, and communicates with both the plurality of transducers and the diaphragm of the target interface, and functions as an acoustical coupler to combine the waveforms formed by the plurality of transducers to form the interference wave.

Still yet another object of the present invention is to provide a neoplasm cell destruction device utilizing low frequency sound waves to disrupt or displace cellular materials wherein the target interface further includes a steering tube that enters the internal chamber in the catheter of the target interface, through a steering tube port in the catheter of the target interface, and extends to the distal treatment end of the catheter of the target interface, with a proximal end of the steering tube of the target interface disposed externally to the internal chamber in the catheter of the target interface.

Yet still yet another object of the present invention is to provide a neoplasm cell destruction device utilizing low frequency sound waves to disrupt or displace cellular materials wherein the target interface further includes steering apparatus that passes through the steering tube of the target interface, and functions to steer the catheter of the target interface through the lumen in the body of the patient to at least close proximity to the neoplastic cells.

Still yet another object of the present invention is to provide a neoplasm cell destruction device utilizing low frequency sound waves to disrupt or displace cellular materials wherein the steering apparatus of the target interface is bimetallic and is operatively connected to the controller.

Yet still yet another object of the present invention is to provide a neoplasm cell destruction device utilizing low frequency sound waves to disrupt or displace cellular materials wherein the target interface further includes a viewing tube that enters the internal chamber in the catheter of the target interface, through a viewing tube port in the catheter of the target interface, and extends to the distal treatment end of the catheter of the target interface, with a proximal end of the viewing tube of the target interface disposed externally to the internal chamber in the catheter of the target interface.

Still yet another object of the present invention is to provide a neoplasm cell destruction device utilizing low frequency sound waves to disrupt or displace cellular materials wherein the target interface further includes viewing apparatus that passes through the viewing tube of the target interface, and functions to assist steering the steering apparatus of the target interface and viewing the neoplastic cells being damaged.

Yet still yet another object of the present invention is to provide a neoplasm cell destruction device utilizing low frequency sound waves to disrupt or displace cellular materials wherein the viewing apparatus of the target interface is fiber optical.

Still yet another object of the present invention is to provide a method of using a neoplasm cell destruction device to destruct neoplastic cells with resonant frequencies by utilizing low frequency sound waves to damage and ultimately destruct the neoplastic cells without destructing surrounding healthy cells by virtue of the neoplastic cells trading in their ability to heal themselves if damaged in return for uncontrollable reproduction whereas the healthy cells can repair themselves if damaged and thereby eliminating the need for location finding apparatus, the method includes the steps of: activating a controller of the neoplasm cell destruction device by use of a user interface of the neoplasm cell destruction device which is in electrical communication with the controller; generating timing and control signals by the controller; activating selectively a plurality of signal generators of the neoplasm cell destruction device by the timing and controls signals generated by the controller wherein the controller is in electrical communication with the plurality of signal generators; generating signals by the plurality of signal generators; amplifying the signals generated by the plurality of signal generators, by a plurality of amplifiers of the neoplasm cell destruction device to form amplified signals wherein each amplifier of the plurality of amplifiers is in electrical communication with a respective signal generator of the plurality of signal generators; forming waveforms that are low frequency sound waves from the amplified signals by a plurality of transducers of the neoplasm cell destruction device wherein each transducer of the plurality of transducers is in electrical communication with a respective amplifier of the plurality of amplifiers; combining the waveforms emanating from the plurality of transducers, in a target interface of the neoplasm cell destruction device, to form an interference wave which is a low frequency sound wave; impacting the interference wave upon the neoplasmous cells; and, damaging and ultimately destructing the neoplastic cells without destructing the surrounding healthy cells by virtue of the neoplastic cells trading in their ability to heal themselves if damaged in return for uncontrollable reproduction whereas the healthy cells can repair themselves if damaged and thereby eliminating the need for location finding apparatus.

Yet still yet another object of the present invention is to provide a method of using a neoplasm cell destruction device to destruct neoplastic cells with resonant frequencies by utilizing low frequency sound waves to damage and ultimately destruct the neoplastic cells without destructing surrounding healthy cells by virtue of the neoplastic cells trading in their ability to heal themselves if damaged in return for uncontrollable reproduction whereas the healthy cells can repair themselves if damaged and thereby eliminating the need for location finding apparatus, the method further includes the step of emanating a feedback wave from the neoplastic cells when the neoplastic cells are impacted upon by the interference wave.

Still yet another object of the present invention is to provide a method of using a neoplasm cell destruction device to destruct neoplastic cells with resonant frequencies by utilizing low frequency sound waves to damage and ultimately destruct the neoplastic cells without destructing surrounding healthy cells by virtue of the neoplastic cells trading in their ability to heal themselves if damaged in return for uncontrollable reproduction whereas the healthy cells can repair themselves if damaged and thereby eliminating the need for location finding apparatus wherein the method further includes the steps of sensing the feedback wave by a feedback sensor of the neoplasm cell destruction device, which is disposed in close proximity to the target interface, and which is in electrical communication with the controller; generating a feedback signal by the feedback sensor in response to the feedback wave sensed; receiving the feedback signal by the controller; comparing continually the feedback signal with the interference wave; and, adjusting automatically the plurality of signal generators, accordingly, until the interference wave is at the resonant frequencies of the neoplastic cells so as to maximize damage to the neoplastic cells.

Finally, yet still yet another object of the present invention is to provide a method of using a neoplasm cell destruction device to destruct neoplastic cells with resonant frequencies by utilizing low frequency sound waves to damage and ultimately destruct the neoplastic cells without destructing surrounding healthy cells by virtue of the neoplastic cells trading in their ability to heal themselves if damaged in return for uncontrollable reproduction whereas the healthy cells can repair themselves if damaged and thereby eliminating the need for location finding apparatus wherein the method further includes the steps of sensing the feedback wave by a feedback sensor of the neoplasm cell destruction device, which is disposed in close proximity to the target interface, and which is in electrical communication with the plurality of signal generators; generating a feedback signal by the feedback sensor in response to the feedback wave sensed; receiving said feedback signal by the plurality of signal generators; and, adjusting manually the plurality of signal generators, accordingly, until the interference wave is at the resonant frequencies of the neoplastic cells so as to maximize damage to the neoplastic cells.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures on the drawing are briefly described as follows.

DETAILED DESCRIPTION OF THE PREFERRED EMBODIMENT

Figure 1A:
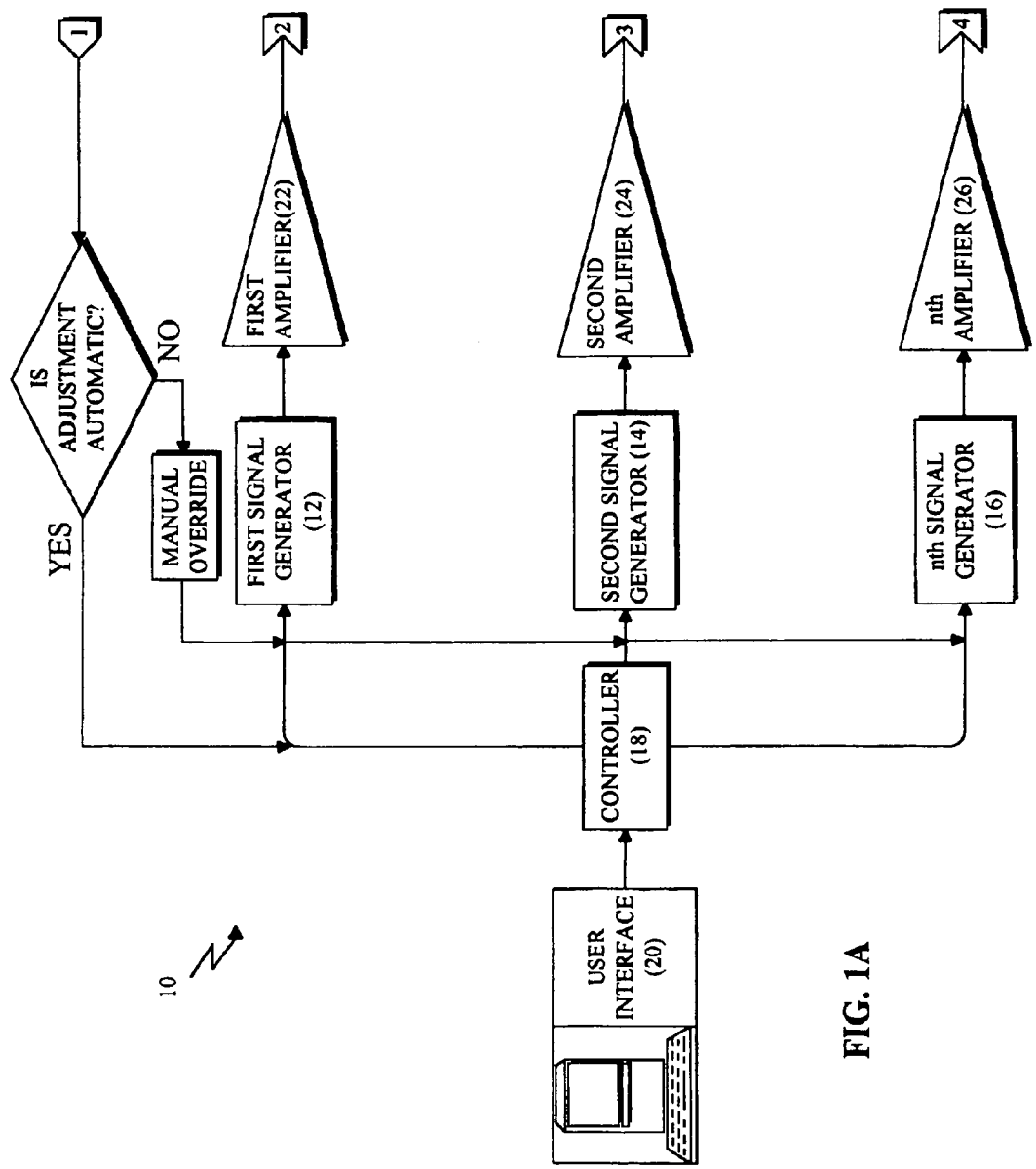
FIGS. 1A to 1C is a block diagram of the present invention.
Figure 1B:
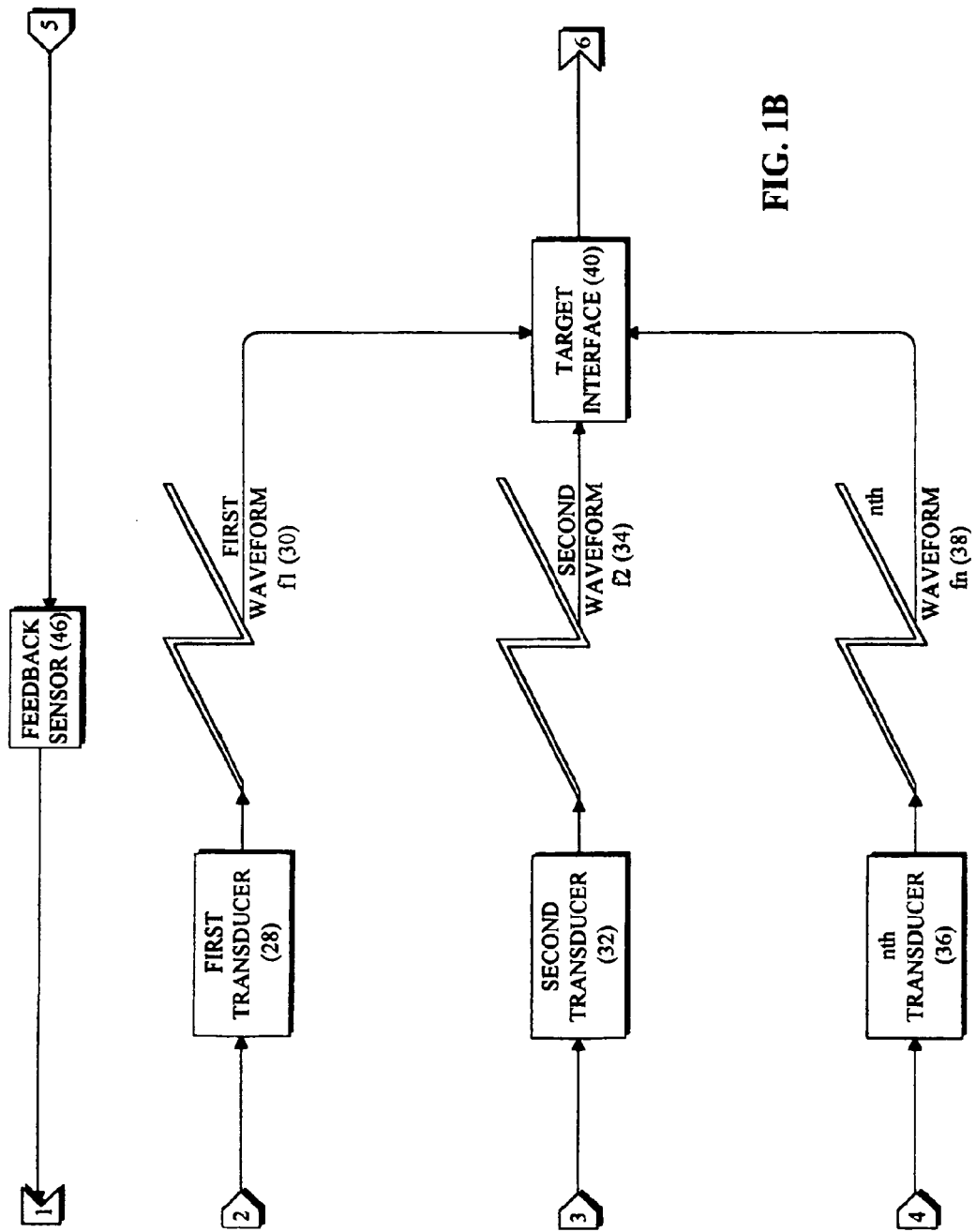
Figure 1C:
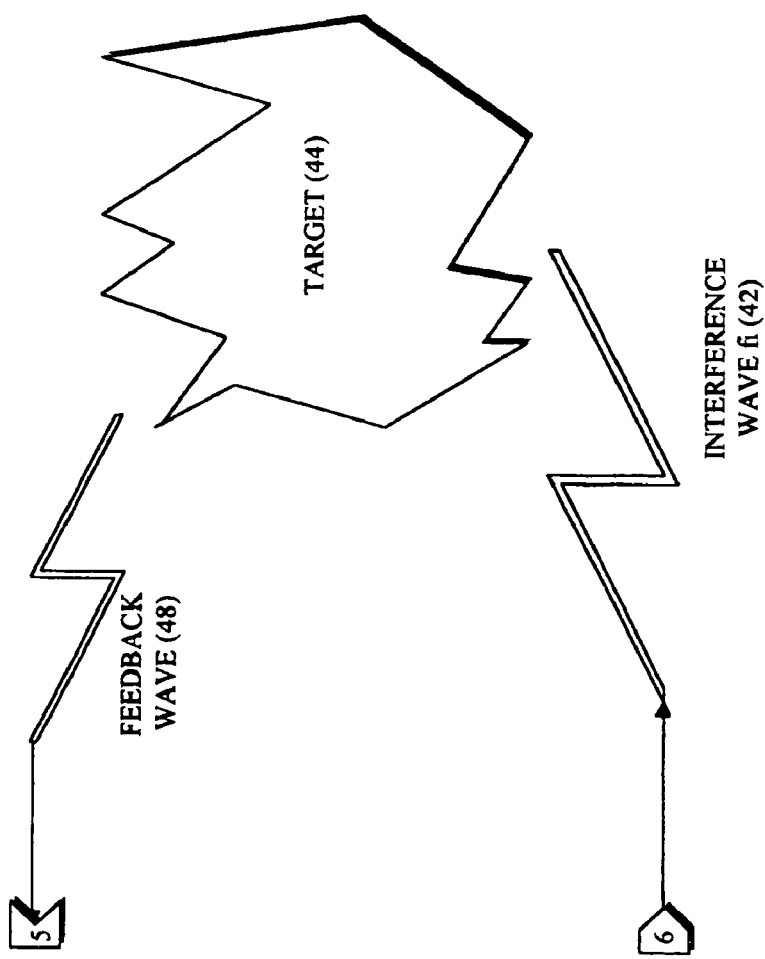
Figure 2A:
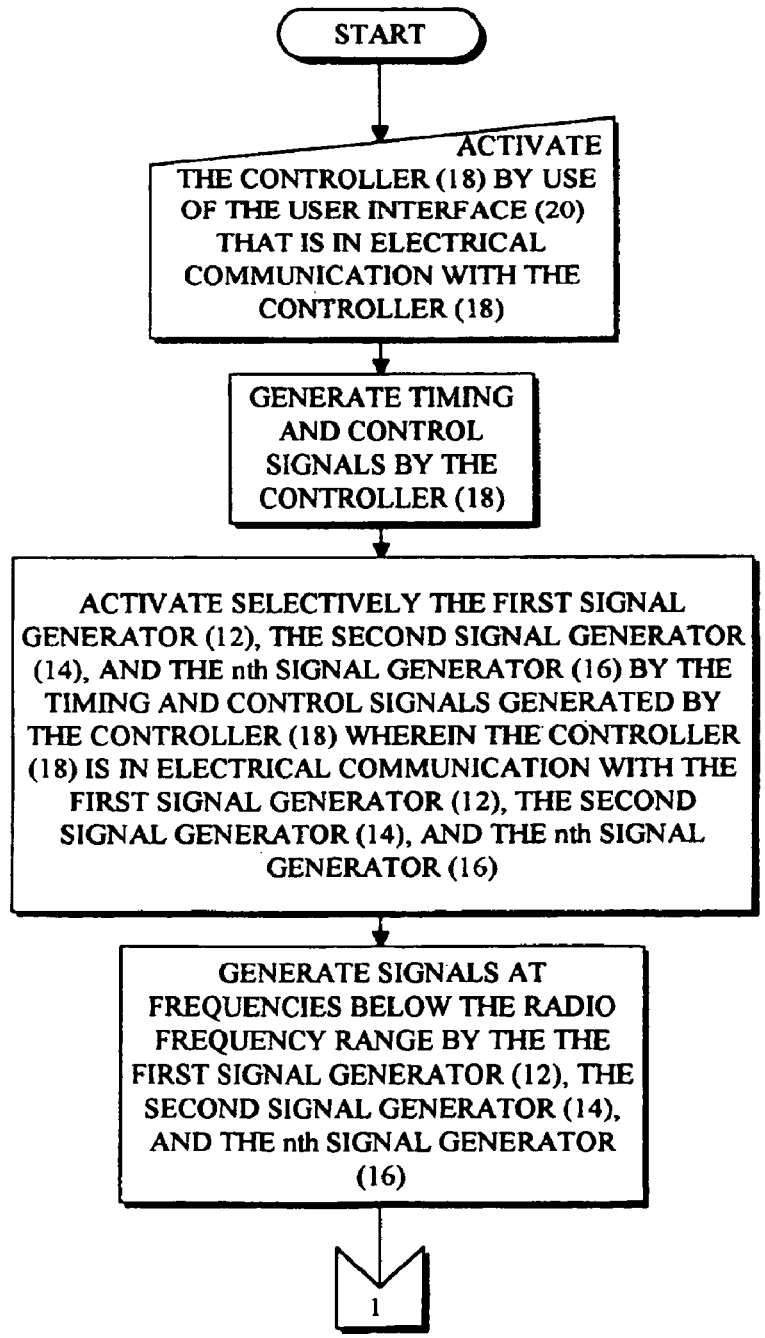
FIGS. 2A to 2E is a flow chart of the present invention.
Figure 2B:
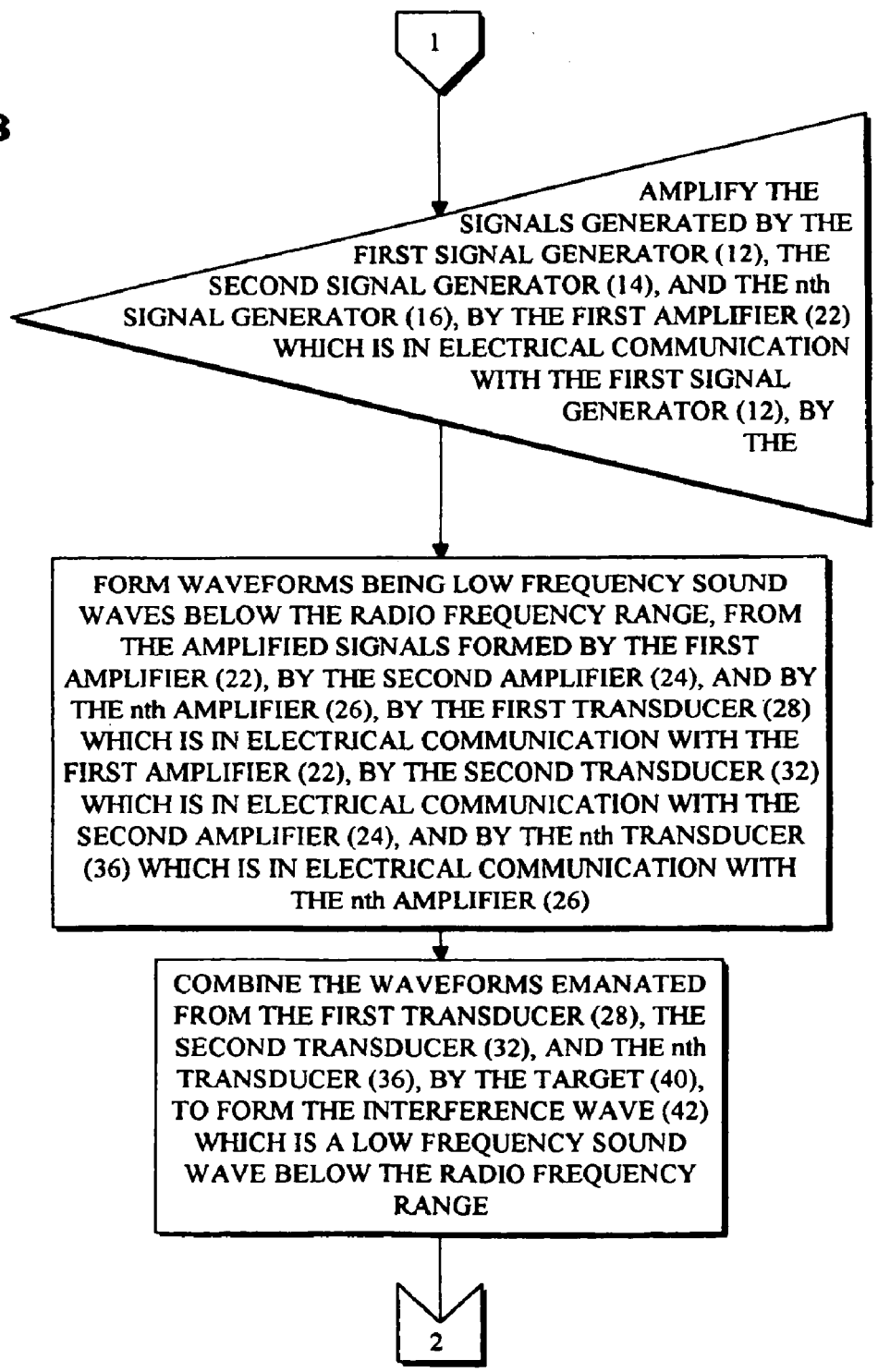
Figure 2C:
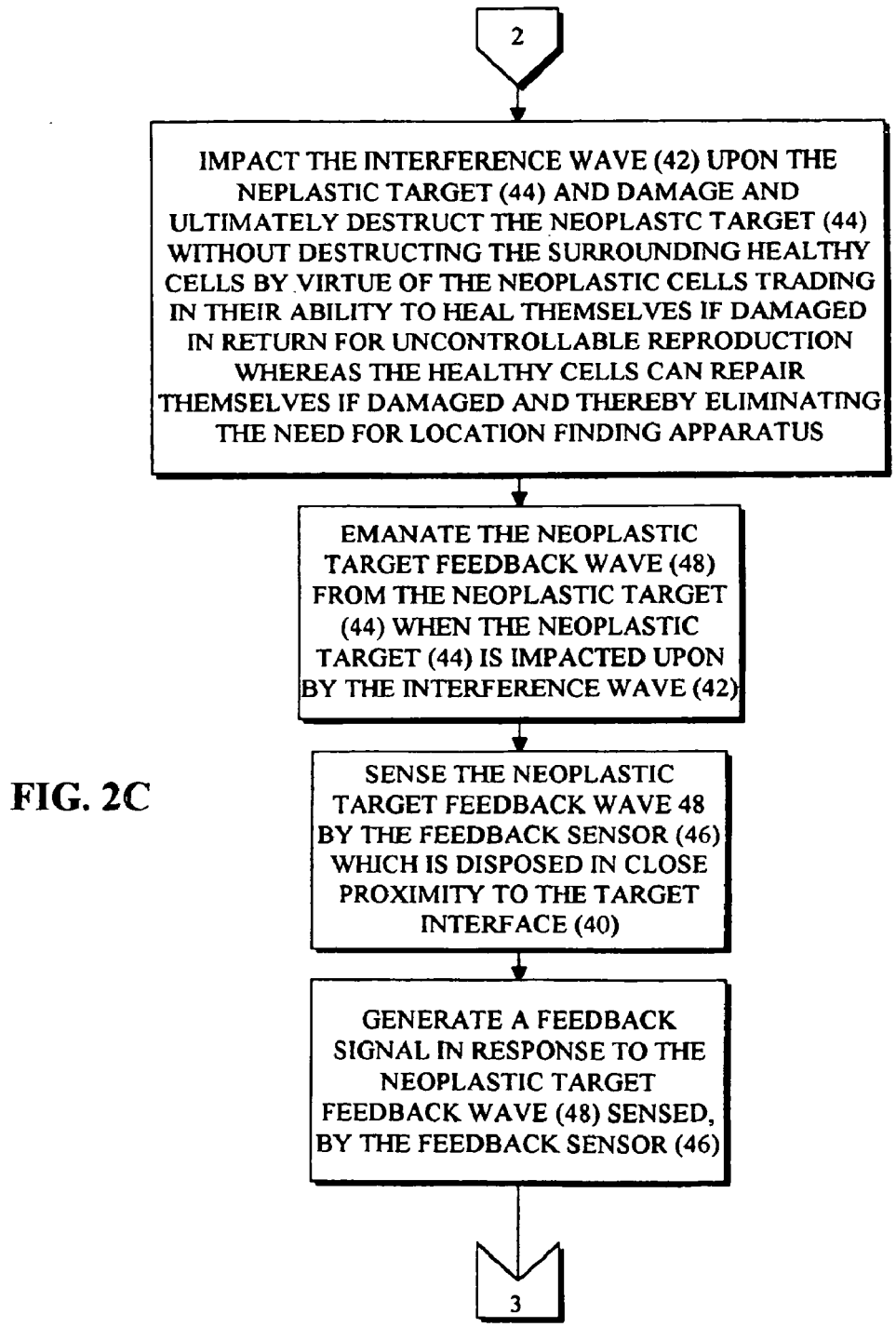
Figure 2D:
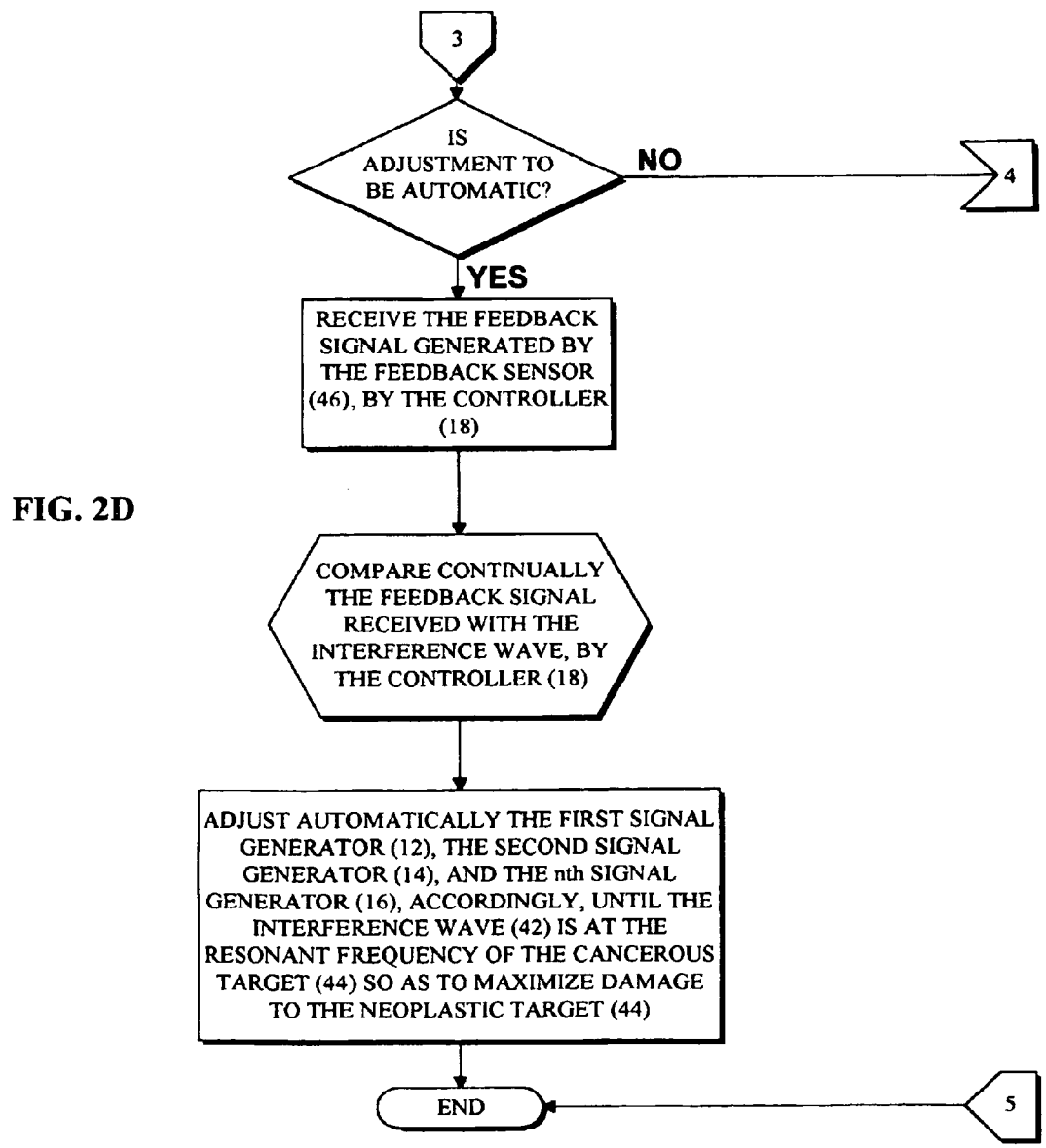
Figure 2E:
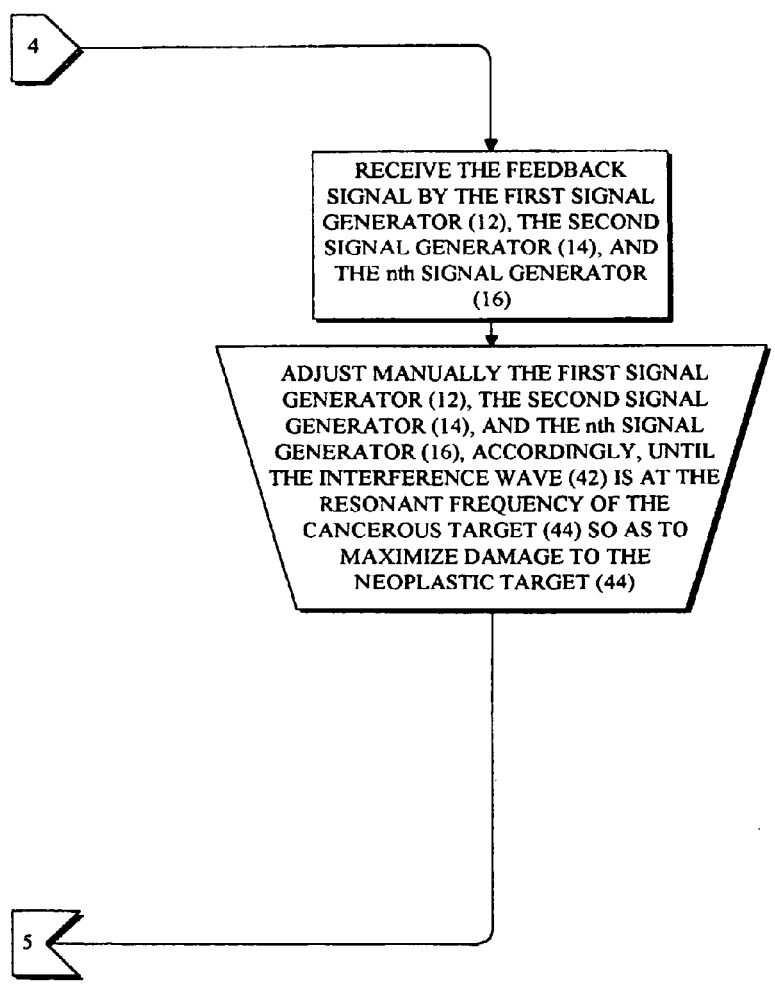

Referring now to the figures in which like numerals indicate like parts and particularly to FIGS. 1A to 1C, which is a block diagram of the present invention, the neoplasm cell destruction device utilizing low frequency sound waves to disrupt or displace cellular materials of the present invention is shown generally at 10.

The neoplasm call destruction device utilizing low frequency sound waves to disrupt or displace cellular materials 10 includes a plurality of signal generators.

The plurality of signal generators include a first signal generator 12 that generates a first signal at a frequency $f_1$ which is a low frequency sound wave.

The plurality of signal generators further includes a second signal generator 14 that generates a second signal at a frequency $f_2$ which is a low frequency sound wave.

The plurality of signal generators further include an nth signal generator 16 that generates an nth signal at an nth frequency $f_n$ which is a low frequency sound wave wherein n is any integer from 3 to $\infty$.

The neoplasm cell destruction device utilizing low frequency sound waves to disrupt or displace cellular materials 10 further includes a controller 18 that is in electrical communication with, and generates timing and control signals to selectively activate, the first signal generator 12, the second signal generator 14, and the nth signal generator 16.

The controller 18 can be, inter alia, a microprocessor.

The neoplasm cell destruction device utilizing low frequency sound waves to disrupt or displace cellular materials 10 further includes a user interface 20 that is in electrical communication with the controller 18.

The user interface 20 can be, inter alia, a keyboard and display or any other form thereof without departing in any way from the spirit of the present invention.

The neoplasm cell destruction device utilizing low frequency sound waves to disrupt or displace cellular materials 10 further includes a plurality of amplifiers.

The plurality of amplifiers include a first amplifier 22 that is in electrical communication with the first signal generator 12 and amplifies the first signal generated thereby to form an amplified first signal.

The plurality of amplifiers further include a second amplifier 24 that is in electrical communication with the second signal generator 14 and amplifies the second signal generated thereby to form an amplified second signal.

The plurality of amplifiers further include an nth amplifier 26 that is in electrical communication with the nth signal generator 16 and amplifies the nth signal generated thereby to form an amplified nth signal wherein n is an integer from 3 to $\infty$.

The neoplasm cell destruction device utilizing low frequency sound waves to disrupt or displace cellular materials 10 further includes a plurality of transducers.

The plurality of transducers includes a first transducer 28 that is in electrical communication with the first amplifier 22, and is driven by the amplified first signal to form a first waveform 30 which is a low frequency sound wave.

The plurality of transducers further includes a second transducer 32 that is in electrical communication with the second amplifier 24, and is driven by the amplified second signal to form a second waveform 34 which is a low frequency sound wave.

The plurality of transducers further include an nth transducer 36 that is in electrical communication with the nth amplifier 26, and is driven by the amplified nth signal to form an nth waveform 38 which is a low frequency sound wave wherein n is any integer from 3 to ∞.

The neoplasm cell destruction device utilizing low frequency sound waves to disrupt or displace cellular materials 10 further includes a target interface 40 that combines the first waveform 30, the second waveform 34, and the nth waveform 38 to form an interference wave 42 at a frequency $f_i$ which is a low frequency sound wave. The interference wave 42 is impactable upon a neoplastic target 44, which has a resonant frequency, and damages the neoplasmous target 44 by one of disrupting and displacing the cellular material of the neoplastic target 44 which leads to the ultimate death of the neoplastic target 44 by virtue of neoplasm cells trading in their ability to heal themselves in return for uncontrollable reproduction.

It is to be understood that the first waveform 30, the second waveform 34, and the nth waveform 38 are preferably different, and when combined provide a synergistic effect in producing the interference wave 42.

The neoplasm cell destruction device utilizing low frequency sound waves to disrupt or displace cellular materials 10 further includes a feedback sensor 46 that is disposed in close proximity to the target interface 40, and is in electrical communication with the controller 18.

The feedback sensor 46 receives a neoplastic target feedback wave 48 emanating from the neoplastic target 44, when the neoplastic target 44 is impacted upon by the interference wave 42, and generates a feedback signal in response thereto that is received by the controller 18 which in turn continually compares the feedback signal to the interference wave 42 and automatically adjusts the first signal generator 12, the second signal generator 14, and the nth signal generator 16, accordingly, until the interference wave 42 is at the resonant frequency of the neoplastic target 44 so as to maximize damage to the neoplastic target 44.

It is to be understood that the controller 18 can be manually overrided and the feedback signal from the feedback sensor 46 would then go directly to the first signal generator 12, the second signal generator 14, and the nth signal generator 16 which would be manually adjusted, accordingly, until the interference wave 42 is at the resonant frequency of the neoplastic target 44 so as to maximize damage to the neoplastic target 44.

The method of operation of the neoplasm cell destruction device utilizing low frequency sound waves to disrupt or displace cellular materials 10 can best be seen in FIGS. 2A to 2E, which is a flow chart of the present invention, and as such will be discussed with reference thereto.

STEP 1: Activate the controller 18 by use of the user interface 20 that is in electrical communication with the controller 18.

STEP 2: Generate timing and control signals by the controller 18.

STEP 3: Activate selectively the first signal generator 12, the second signal generator 14, and the nth signal generator 16 by the timing and controls signals generated by the controller 18 wherein the controller 18 is in electrical communication with the first signal generator 12, the second signal generator 14, and the nth signal generator 16.

STEP 4: Generate signals by the first signal generator 12, the second signal generator 14, and the nth signal generator 16.

STEP 5: Amplify the signals generated by the first signal generator 12, the second signal generator 14, and the nth signal generator 16, by the first amplifier 22 which is in electrical communication with the first signal generator 12, by the second amplifier 24 which is in electrical communication with the second signal generator 14, and by the nth amplifier 26 which is in electrical communication with the nth signal generator 16, to form amplified signals.

STEP 6: Form waveforms being low frequency sound waves from the amplified signals formed by the first amplifier 22, by the second amplifier 24, and by the nth amplifier 26, by the first transducer 28 which is in electrical communication with the first amplifier 22, by the second transducer 32 which is in electrical communication with the second amplifier 24, and by the nth transducer 36 which is in electrical communication with the nth amplifier 26.

STEP 7: Combine the waveforms emanated from the first transducer 28, the second transducer 32, and the nth transducer 36, by the target interface 40, to form the interference wave 42 which is a low frequency sound wave.

STEP 8: Impact the interference wave 42 upon the neoplastic target 44 and damage and ultimately destruct the neoplastic target 44 without destructing the surrounding healthy cells by virtue of the neoplastic cells trading in their ability to heal themselves if damaged in return for uncontrollable reproduction whereas the healthy cells can repair themselves if damaged and thereby eliminating the need for location finding apparatus.

STEP 9: Emanate the neoplastic target feedback wave 48 from the neoplastic target 44 when the neoplastic target 44 is impacted upon by the interference wave 42.

STEP 10: Sense the neoplastic target feedback wave 48 by the feedback sensor 46 which is disposed in close proximity to the target interface 40.

STEP 11: Generate a feedback signal in response to the neoplastic target feedback wave 48 sensed, by the feedback sensor 46.

STEP 12: Receive the feedback signal generated by the feedback sensor 46, by the controller 18.

STEP 13: Compare continually the feedback signal received with the interference wave 42, by the controller 18.

STEP 14: Adjust automatically the first signal generator 12, the second signal generator 14, and the nth signal generator 16, accordingly, until the interference wave 42 is at the resonant frequency of the neoplastic target 44 so as to maximize damage to the neoplastic target 44.

It is to be understood that the automatic adjusting being accomplished by STEP 12 to STEP 14, supra, can be manually overrided and replaced with the manual steps, infra.

STEP 12: Receive the feedback signal by the first signal generator 12, the second signal generator 14, and the nth signal generator 16.

STEP 13: Adjust manually the first signal generator 12, the second signal generator 14, and the nth signal generator 16, accordingly, until the interference wave 42 is at the resonant frequency of the neoplastic target 44 so as to maximize damage to the neoplastic target 44.

Figure 3:
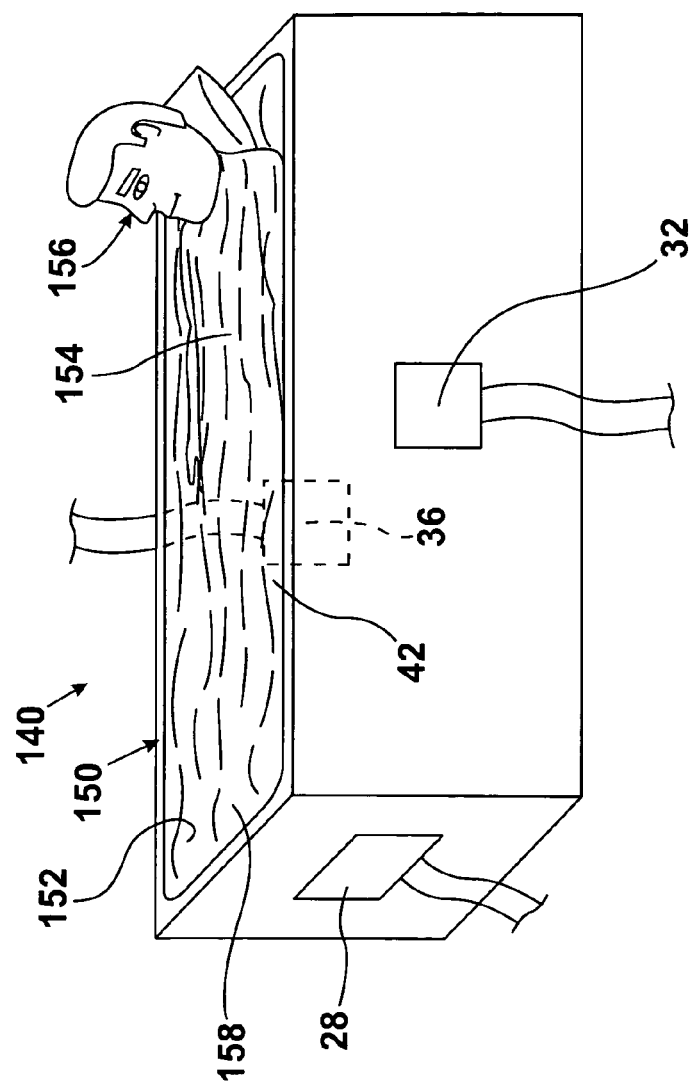
FIG. 3 is a diagrammatic perspective view of a first embodiment of the target interface of FIG. 1, utilized to treat the entire body of a patient.

The configuration of a first embodiment of a target interface 140 can best be seen in FIG. 3, which is a diagrammatic perspective view of a first embodiment of the target interface of FIG. 1, utilized to treat the entire body of a patient, and as such will be discussed with reference thereto.

The target interface 140 includes a target interface tub 150 that defines a target interface tub internal chamber 152 in which a patient body 154 of a patient 156 is placeable when the neoplastic target 44 is wide spread throughout the patient body 154 of the patient 156.

The first transducer 28, the second transducer 32, and the nth transducer 36 are disposed on the target interface tub 150 of the target interface 140, with the first waveform 30, the second waveform 34, and the nth waveform 38 emanating therefrom into the target interface tub internal chamber 152 in the target interface tub 150 of the target interface 140.

The target interface 140 further includes a target interface liquid 158 that is contained in the target interface tub internal chamber 152 in the tub 150 of the target interface 140, and communicates with the first transducer 28, the second transducer 32, the nth transducer 36, and the patient body 154 of the patient 156, and functions as an acoustical coupler to combine the first waveform 30, the second waveform 34, and the nth waveform 38 to form the interference wave 42.

Figure 4:
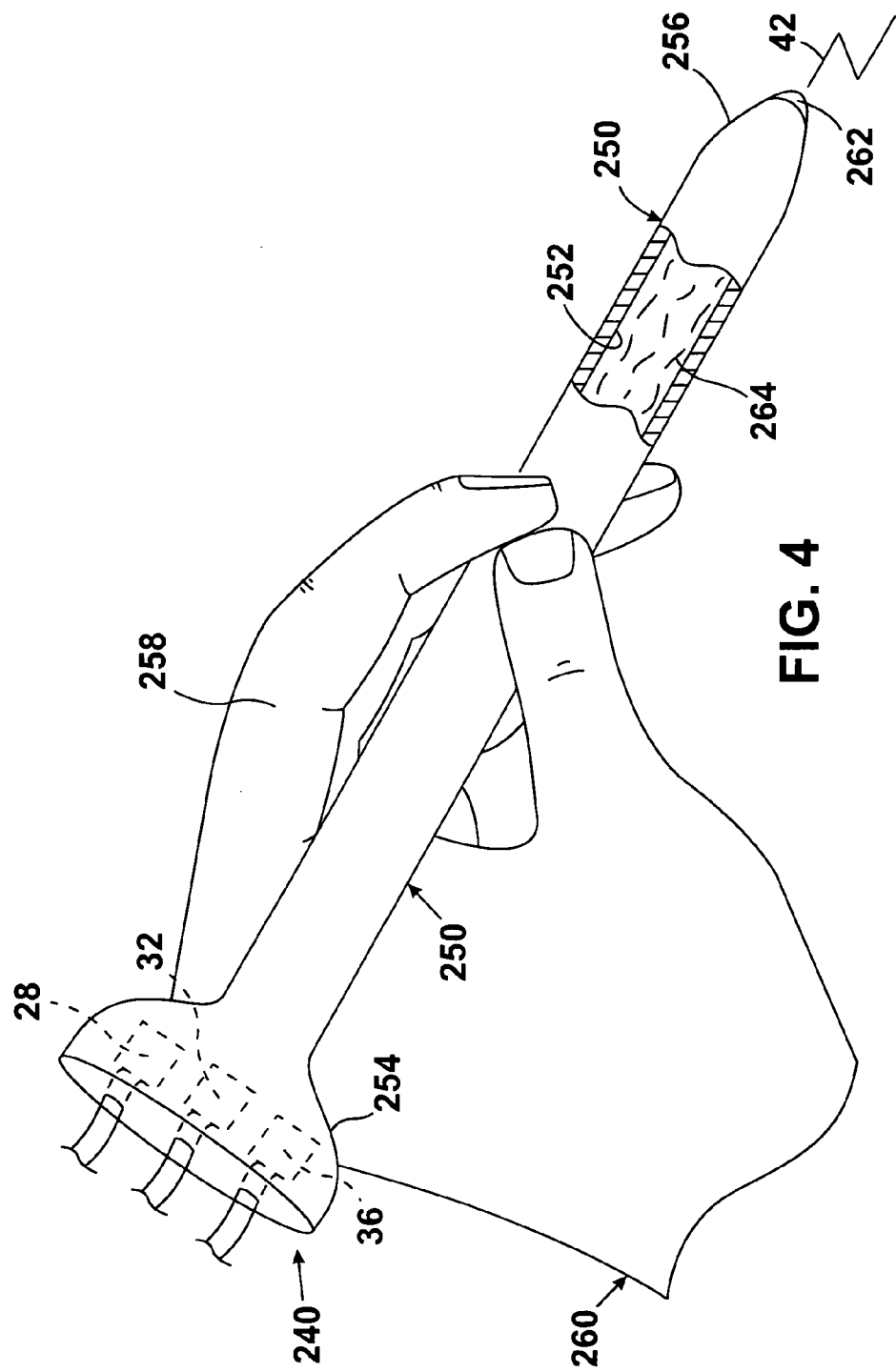
FIG. 4 is a diagrammatic perspective view of a second embodiment of the target interface of FIG. 1, utilized to treat a small area of a patient.

The configuration of a second embodiment of a target interface 240 can best be seen in FIG. 4, which is a diagrammatic perspective view of a second embodiment of the target interface of FIG. 1, utilized to treat a small area of a patient, and as such will be discussed with reference thereto.

The target interface 240 includes a target interface hollow, elongated, and slender, hand-held tubular body 250 that contains a target interface body internal chamber 252, and has a target interface body wide proximal end 254 and a target interface body tapered distal treatment end 256, and is holdable in, and orientatably controllable by, a user hand 258 of a user 260.

The target interface hollow, elongated, and slender, handheld tubular body 250 of the target interface 240 is preferably plastic or metal.

The first transducer 28, the second transducer 32, and the nth transducer 36 are disposed at the target interface body wide proximal end 254 of the target interface hollow, elongated, and slender, hand-held tubular body 250 of the target interface 240, with the first waveform 30, the second waveform 34, and the nth waveform 38 emanating therefrom into the target interface body internal chamber 252 in the target interface hollow, elongated, and slender, hand-held tubular body 250 of the target interface 240.

The target interface 240 further includes a target interface diaphragm 262 that is disposed at, and closes, the target interface body tapered distal treatment end 256 of the target interface hollow, elongated, and slender, hand-held tubular body 250 of the target interface 240, and concentrates the interference wave 42.

The target interface diaphragm 262 of the target interface 240 communicates with the target interface body internal chamber 252 in the target interface hollow, elongated, and slender, hand-held tubular body 250 of the target interface 240, and is contactable at least in close proximity to the neoplastic target 44 when the neoplastic target 44 is contained in a small area in a body of a patient and pinpoint accuracy is required.

The target interface 240 further includes a target interface liquid 264 that is contained in the target interface body internal chamber 252 in the target interface hollow, elongated, and slender, hand-held tubular body 250 of the target interface 240, and communicates with the first transducer 28, the second transducer 32, the nth transducer 36, and the target interface diaphragm 262 of the target interface 240, and functions as an acoustical coupler to combine the first waveform 30, the second waveform 34, and the nth waveform 38 to form the interference wave 42.

Figure 5:
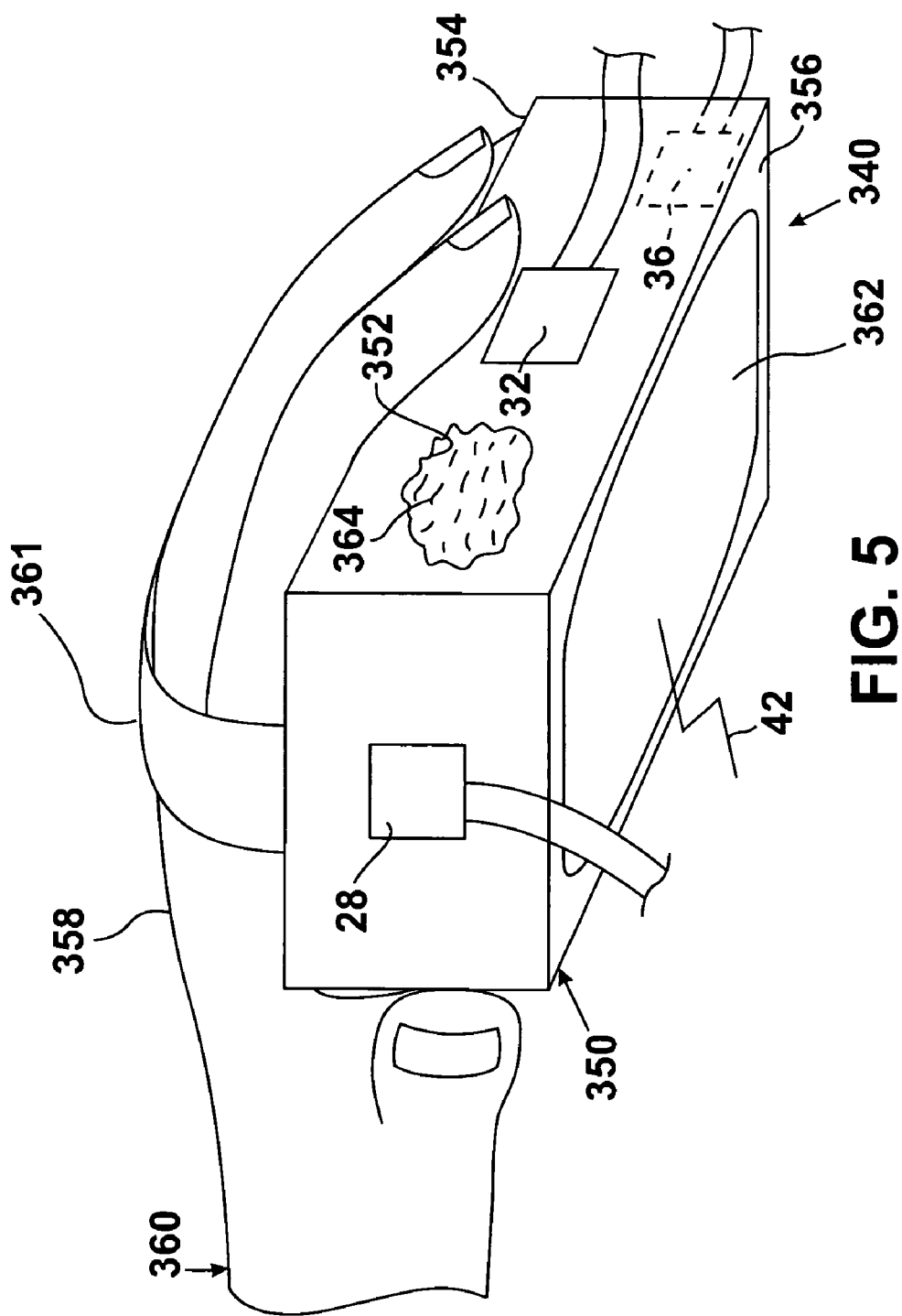
FIG. 5 is a diagrammatic perspective view of a third embodiment of the target interface of FIG. 1, utilized to treat a large area of a patient.

The configuration of a third embodiment of a target interface 340 can best be seen in FIG. 5, which is a diagrammatic perspective view of a third embodiment of the target interface of FIG. 1, utilized to treat a large area of a patient, and as such will be discussed with reference thereto.

The target interface 340 includes a target interface hollow and hand-held body 350 that contains a target interface body internal chamber 352, and has a target interface body upper wall 354 and a target interface body lower treatment wall 356, and is holdable in a user hand 358 of a user 360 that is passable through a target interface upper wall loop 361 of the target interface 340 that is disposed on the target interface body upper wall 354 of the target interface hollow and hand-held body 350 of the target interface 340.

The target interface hollow and hand-held body 350 of the target interface 340 is preferably plastic or metal.

The first transducer 28, the second transducer 32, and the nth transducer 36 are disposed at any convenient location of the of the target interface hollow and hand-held body 350 of the target interface 340 that is not obstructive to the target interface upper wall loop 361 of the target interface 340, with the first waveform 30, the second waveform 34, and the nth waveform 38 emanating therefrom into the target interface body internal chamber 352 in the target interface hollow and hand-held body 350 of the target interface 340.

The target interface 340 further includes a target interface diaphragm 362 that is disposed at, and closes, the target interface body lower treatment wall 356 of the target interface hollow and hand-held body 350 of the target interface 340, and distributes the interference wave 42.

The target interface diaphragm 362 of the target interface 340 communicates with the target interface body internal chamber 352 in the target interface hollow and hand-held body 350 of the target interface 340, and is contactable at least in close proximity to the neoplastic target 44 when the neoplastic target 44 is contained in a large area in a body of a patient.

The target interface 340 further includes a target interface liquid 364 that is contained in the target interface body internal chamber 352 in the target interface hollow and hand-held body 350 of the target interface 340, and communicates with the first transducer 28, the second transducer 32, the nth transducer 36, and the target interface diaphragm 362 of the target interface 340, and functions as an acoustical coupler to combine the first waveform 30, the second waveform 34, and the nth waveform 38 to form the interference wave 42.

Figure 6:
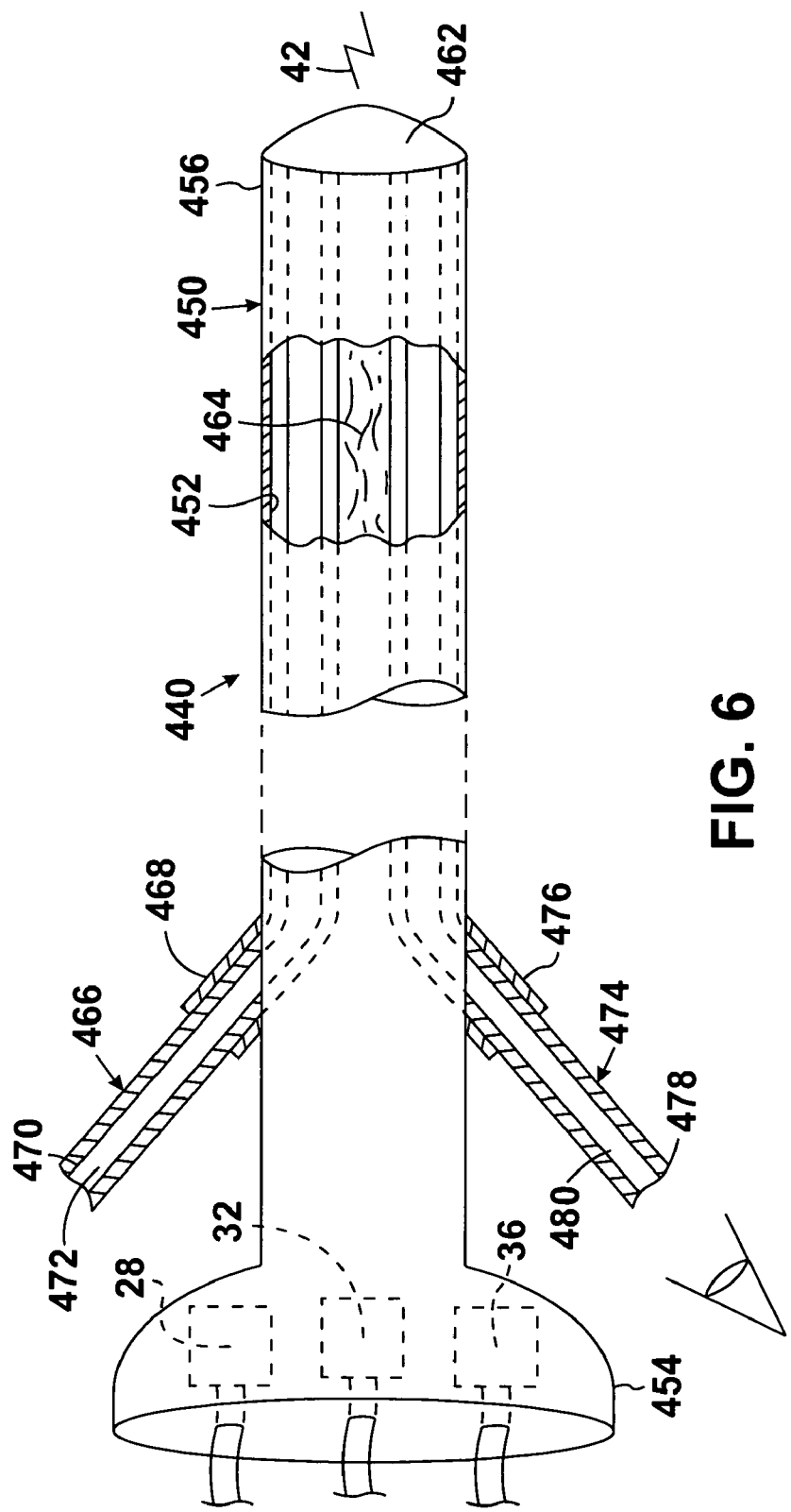
FIG. 6 is a diagrammatic perspective view of a fourth embodiment of the target interface of FIG. 1, utilized to treat a lumen of a patient.

The configuration of a fourth embodiment of a target interface 440 can best be seen in FIG. 6, which is a diagrammatic perspective view of a fourth embodiment of the target interface of FIG. 1, utilized to treat a lumen of a patient, and as such will be discussed with reference thereto.

The target interface 440 includes a target interface catheter 450 that contains a target interface catheter internal chamber 452, and has a target interface catheter wide proximal end 454 and a target interface catheter distal treatment end 456.

The first transducer 28, the second transducer 32, and the nth transducer 36 are disposed at the target interface catheter wide proximal end 454 of the target interface catheter 450 of the target interface 440, with the first waveform 30, the second waveform 34, and the nth waveform 38 emanating therefrom into the target interface catheter internal chamber 452 in the target interface catheter 450 of the target interface 440.

The target interface 440 further includes a target interface diaphragm 462 that is disposed at, and closes, the target interface catheter distal treatment end 456 of the target interface catheter 450 of the target interface 440, and concentrates the interference wave 42.

The target interface diaphragm 462 of the target interface 440 communicates with the target interface catheter internal chamber 452 in the target interface catheter 450 of the target interface 440, and is contactable at least in close proximity to the neoplastic target 44 when the neoplastic target 44 is contained in a lumen in a body of a patient.

The target interface 440 further includes a target interface liquid 464 that is contained in the target interface catheter internal chamber 452 in the target interface catheter 450 of the target interface 440, and communicates with the first transducer 28, the second transducer 32, the nth transducer 36, and the target interface diaphragm 462 of the target interface 440, and functions as an acoustical coupler to combine the first waveform 30, the second waveform 34, and the nth waveform 38 to form the interference wave 42.

The target interface 440 further includes a target interface steering tube 466 that enters the target interface catheter internal chamber 452 in the target interface catheter 450 of the target interface 440, through a target interface catheter steering tube port 468 in the target interface catheter 450 of the target interface 440, and extends to the target interface catheter distal treatment end 456 of the target interface catheter 450 of the target interface 440, with a target interface steering tube proximal end 470 of the target interface steering tube 466 of the target interface 440 disposed externally to the target interface catheter internal chamber 452 in the target interface catheter 450 of the target interface 440.

The target interface 440 further includes target interface steering means 472 that passes through the target interface steering tube 466 of the target interface 440, and functions to steer the target interface catheter 450 of the target interface 440 through the lumen in the body of the patient to at least close proximity to the neoplastic target 44.

The target interface steering means 472 of the target interface 440 is preferably bimetallic and is operatively connected to the controller 18.

The target interface 440 further includes a target interface viewing tube 474 that enters the target interface catheter internal chamber 452 in the target interface catheter 450 of the target interface 440, through a target interface catheter viewing tube port 476 in the target interface catheter 450 of the target interface 440, and extends to the target interface catheter distal treatment end 456 of the target interface catheter 450 of the target interface 440, with a target interface viewing tube proximal end 478 of the target interface viewing tube 474 of the target interface 440 disposed externally to the target interface catheter internal chamber 452 in the target interface catheter 450 of the target interface 440.

The target interface 440 further includes target interface viewing means 480 that passes through the target interface viewing tube 474 of the target interface 440, and functions to assist steering the target interface steering means 472 of the target interface 440 and view the neoplastic target 44 being damaged.

The target interface viewing means 480 of the target interface 440 is preferably fiber optical.

It will be understood that each of the elements described above, or two or more together, may also find a useful application in other types of constructions differing from the types described above.

While the invention has been illustrated and described as embodied in a neoplasm cell destruction device utilizing low frequency sound waves to disrupt or displace cellular materials, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A neoplasm cell destruction device utilizing low frequency sound waves to do at least one of disrupt and displace cellular materials in neoplastic cells having resonant frequencies so as to damage and ultimately destruct the neoplastic cells without destructing surrounding healthy cells by virtue of the neoplastic cells trading in their ability to heal themselves if damaged in return for uncontrollable reproduction whereas the healthy cells can repair themselves if damaged and thereby eliminating a need for location finding apparatus, said device comprising:
   a) a plurality of signal generators; each signal generator of said plurality of signal generators generating a signal;
   b) a controller in electrical communication with, and generating timing and control signals for selectively activating, said plurality of signal generators;
   c) a plurality of amplifiers; each amplifier of said plurality of amplifiers being in electrical communication with a respective signal generator of said plurality of signal generators and amplifying said signal generated by said respective signal generator of said plurality of signal generators so as to form an amplified signal;
   d) a plurality of transducers; each transducer of said plurality of transducers being in electrical communication with a respective amplifier of said plurality of amplifiers and being driven by said amplified signal formed by said respective amplifier of said plurality of amplifiers; each transducer of said plurality of transducers forming a waveform being a low frequency sound wave; and
   e) a target interface combining said waveforms formed by said plurality of transducers to form an interference wave which is a low frequency sound wave which is impactable upon the neoplastic cells and damages and ultimately destructs the neoplastic cells without destructing the surrounding healthy cells by virtue of the neoplastic cells trading in their ability to heal themselves if damaged in return for uncontrollable reproduction whereas the healthy cells can repair themselves if damaged and thereby eliminating the need for location finding apparatus; said target interface including a hollow, elongated, and slender, hand-held tubular body containing an internal chamber, and having a wide proximal end and a tapered distal treatment end, and being holdable in, and orientatably controllable by, a hand of a user.

2. The device as defined in claim 1, wherein said controller is a microprocessor.

3. The device as defined in claim 1; further comprising a user interface in electrical communication with said controller.

4. The device as defined in claim 3, wherein said user interface is at least one of a keyboard and a display.

5. The device as defined in claim 1; further comprising a feedback sensor disposed in close proximity to said target interface and being in electrical communication with said controller; said feedback sensor receiving a feedback wave emanating from the neoplastic cells when the neoplastic cells are impacted upon by said interference wave and generating a feedback signal in response thereto that is received by said controller which in turn continually compares the feedback signal received to said interference wave and automatically adjusts each signal generator of said plurality of signal generators, accordingly, until said interference wave is at the resonant frequencies of the neoplastic cells so as to maximize damage to the neoplastic cells.

6. The device as defined in claim 1; further comprising a feedback sensor disposed in close proximity to said target interface and being in electrical communication with each said signal generator of said plurality of signal generators; said feedback sensor receiving a feedback wave emanating from the neoplastic cells when the neoplastic cells are impacted upon by said interference wave and generating a feedback signal in response thereto that is received by each said signal generator of said plurality of signal generators which in turn are manually adjusted, accordingly, until said interference wave is at the resonant frequencies of the neoplastic cells so as to maximize damage to the neoplastic cells.

7. The device as defined in claim 1, wherein said hollow, elongated, and slender, hand-held tubular body of said target interface is one of plastic and metal.

8. The device as defined in claim 1, wherein said plurality of transducers are disposed at said wide proximal end of said hollow, elongated, and slender, hand-held tubular body of said target interface, with each said waveform emanating therefrom into said internal chamber in said hollow, elongated, and slender, hand-held tubular body of said target interface.

9. The device as defined in claim 8, wherein said target interface further includes a diaphragm that is disposed at, and closes, said tapered distal treatment end of said hollow, elongated, and slender, hand-held tubular body of said target interface, and concentrates said interference wave; said diaphragm of said target interface communicates with said internal chamber in said hollow, elongated, and slender, hand-held tubular body of said target interface, and is contactable at least in close proximity to the neoplastic cells when the neoplastic cells are contained in a small area in a body of a patient and pinpoint accuracy is required.

10. The device as defined in claim 9, wherein said target interface further includes a liquid that is contained in said internal chamber in said hollow, elongated, and slender, hand-held tubular body of said target interface, and communicates with both said plurality of transducers and said diaphragm of said target interface, and functions as an acoustical coupler to combine said waveforms formed by said plurality of transducers to form said interference wave.

11. A method of using a neoplasm cell destruction device to destruct neoplastic cells with resonant frequencies by utilizing low frequency sound waves [below the radio frequency range] to damage and ultimately destruct the neoplastic cells without destructing surrounding healthy cells by virtue of the neoplastic cells trading in their ability to heal themselves if damaged in return for uncontrollable reproduction whereas the healthy cells can repair themselves if damaged and thereby eliminating a need for location finding apparatus, said method comprising the steps of:

a) activating a controller of said neoplasm cell destruction device by use of a user interface of said neoplasm cell destruction device that is in electrical communication with said controller;

b) generating timing and control signals by said controller;

c) activating selectively a plurality of signal generators of said neoplasm cell destruction device by said timing and controls signals generated by said controller wherein said controller is in electrical communication with said plurality of signal generators;

d) generating signals [at frequencies below the radio frequency range] by said plurality of signal generators;

e) amplifying said signals generated by said plurality of signal generators by a plurality of amplifiers of said neoplasm cell destruction device to form amplified signals wherein each amplifier of said plurality of amplifiers is in electrical communication with a respective signal generator of said plurality of signal generators;

f) forming waveforms being low frequency sound waves [below the radio frequency range] from said amplified signals, by a plurality of transducers of said neoplasm cell destruction device wherein each transducer of said plurality of transducers is in electrical communication with a respective amplifier of said plurality of amplifiers;

g) combining said waveforms emanating from said plurality of transducers, in a target interface of said neoplasm cell destruction device, to form an interference wave which is a low frequency sound wave [below the radio frequency range];

h) impacting said interference wave upon the neoplastic cells; and

I) damaging and ultimately destructing the neoplastic cells without destructing the surrounding healthy cells by virtue of the neoplastic cells trading in their ability to heal themselves if damaged in return for uncontrollable reproduction whereas the healthy cells can repair themselves if damaged and thereby eliminating the need for location finding apparatus.

12. The method as defined in claim 11; further comprising the steps of:

a) sensing a feedback wave by a feedback sensor of said neoplasm cell destruction device, which is disposed in close proximity to said target interface, and which is in electrical communication with said controller;

b) generating a feedback signal by said feedback sensor in response to said feedback wave sensed;

c) receiving said feedback signal by said controller;

d) comparing continually said feedback signal received by said controller with said interference wave; and e) adjusting automatically said plurality of signal generators, accordingly, until said interference wave is at the resonant frequencies of the neoplastic cells so as to maximize damage to the neoplastic cells.

13. The method as defined in claim 11; further comprising the steps of:

a) sensing a feedback wave by a feedback sensor of said neoplasm cell destruction device which is disposed in close proximity to said target interface and which is in electrical communication with said plurality of signal generators;

b) generating a feedback signal by said feedback sensor in response to said feedback wave sensed;

c) receiving said feedback signal by said plurality of signal generators; and d) adjusting manually said plurality of signal generators, accordingly, until said interference wave is at the resonant frequencies of the neoplastic cells so as to maximize damage to the neoplastic cells.

* * * * *

UNITED STATES PATENT AND TRADEMARK OFFICE
CERTIFICATE OF CORRECTION

| | | |
|---|---|---|
| PATENT NO. | : 7,416,535 B1 | |
| APPLICATION NO. | : 08/777452 | |
| DATED | : August 26, 2008 | |
| INVENTOR(S) | : Kenny | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 5 years.

Signed and Sealed this
Eleventh Day of January, 2011

David J. Kappos
*Director of the United States Patent and Trademark Office*